US 6,613,286 B2

(12) United States Patent
Braun, Sr. et al.

(10) Patent No.: US 6,613,286 B2
(45) Date of Patent: Sep. 2, 2003

(54) APPARATUS FOR TESTING LIQUID/ REAGENT MIXTURES

(76) Inventors: Walter J. Braun, Sr., 7884 S. Argonne Ct., Centennial, CO (US) 80016; Walter J. Braun, Jr., 7884 S. Argonne Ct., Centennial, CO (US) 80016; Steven P. Braun, 7884 S. Argonne Ct., Centennial, CO (US) 80016

( * ) Notice: Subject to any disclaimer, the term of this patent is extended or adjusted under 35 U.S.C. 154(b) by 26 days.

(21) Appl. No.: 09/747,846

(22) Filed: Dec. 21, 2000

(65) Prior Publication Data

US 2002/0081741 A1 Jun. 27, 2002

(51) Int. Cl.[7] ............................................... G01N 33/48
(52) U.S. Cl. .................. 422/102; 422/99; 422/100; 422/103; 422/73; 436/69; 436/180
(58) Field of Search ............................ 422/58, 61, 73, 422/99, 100, 102–103; 436/43, 69, 174, 180

(56) References Cited

U.S. PATENT DOCUMENTS

| 5,629,209 | A | | 5/1997 | Braun, Sr. et al. |
| 5,726,026 | A | * | 3/1998 | Wilding et al. ............ 435/7.21 |

* cited by examiner

Primary Examiner—Lyle A. Alexander
(74) Attorney, Agent, or Firm—Dorr, Carson, Sloan & Birney, P.C.

(57) ABSTRACT

An apparatus for detecting changes in a property of a liquid/reagent mixture comprises a cartridge having a fluid receiving/dispensing reservoir, one or more fluid-receiving chambers, one or more conduit(s) that permit(s) fluid communication between the fluid receiving/dispensing reservoir and the fluid-receiving chamber(s) and wherein the one or more conduits have a constricted passage for increasing the velocity of fluid flow through said constricted passage and thereby more thoroughly mixing the liquid (e.g., human blood) and a reagent (e.g., protamine).

15 Claims, 9 Drawing Sheets

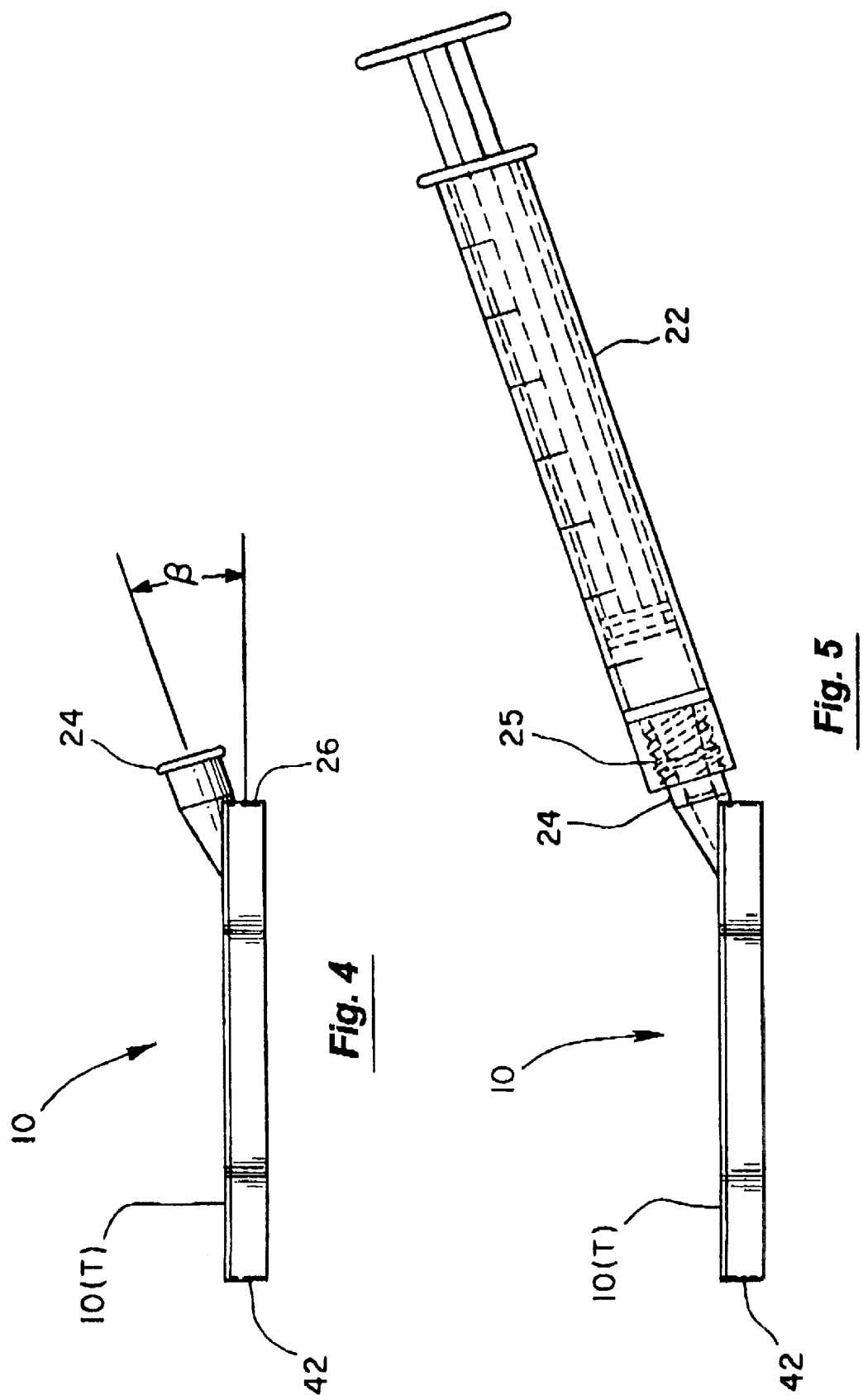

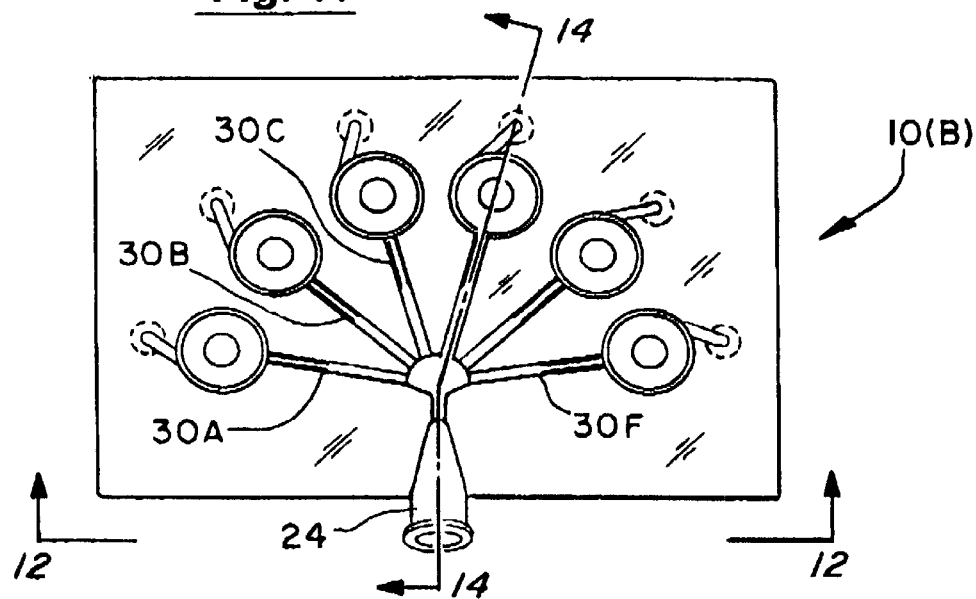
Fig. 11
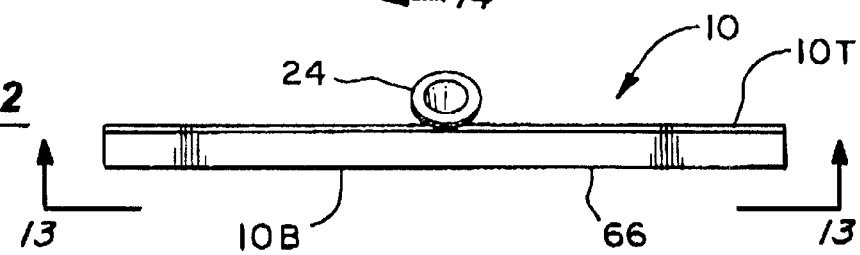
Fig. 12
Fig. 13

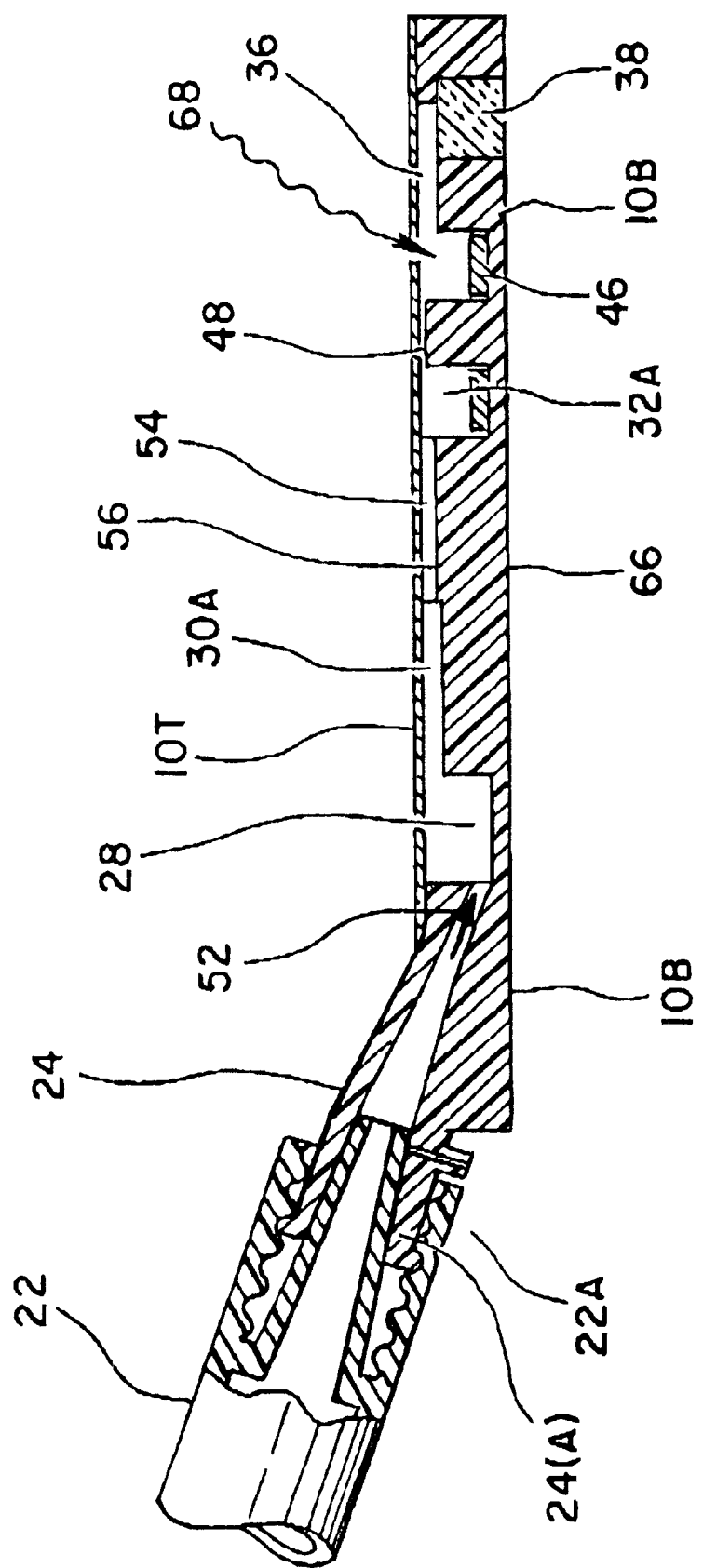

APPARATUS FOR TESTING LIQUID/REAGENT MIXTURES

BACKGROUND OF THE INVENTION

1. Field of the Invention

The present invention generally relates to detection of changes in a property of a liquid that is mixed with one or more reagents. This invention is particularly concerned with detecting changes in viscosity of human blood that is mixed with blood viscosity changing reagents such as heparin and protamine.

2. Statement of Problem

The ability to detect changes in a property of a liquid that has been placed under the influence of a reagent that is capable of changing that property has great practical value. Changes in viscosity, translucence, color, electrical conductivity, optical density, chemical component concentration, and many other properties have been used in a wide variety of tests. For example, detection of changes in the viscosity of liquids such as blood, food products, and various other liquid compositions (e.g., industrial fluids, oil well injection fluids, etc.) form the basis of many very practical tests.

Indeed, the ability to detect changes in the viscosity of human blood can even have life and death consequences. This follows from the fact that a proper balance between normal hemostasis and coagulation or anticoagulation is absolutely essential in maintaining the integrity of the human circulatory system—and in stopping both external and internal bleeding. It is, however, sometimes necessary to modify the natural coagulation system, either by increasing or decreasing the rate of blood coagulation. During open heart surgery for example, a patient is usually supported by a heart/lung bypass machine that provides extracorporeal blood circulation while the heart is stopped. To prevent blood from clotting upon exposure to the bypass system, the patient is treated with high doses of heparin, a naturally occurring substance that significantly prolongs the clotting time of blood. When the time comes to remove the patient from the heart/lung bypass machine, however, it is desirable for the patient's blood to regain its normal coagulation characteristics so that it will again be able to clot and assist in healing incisions and stopping internal or external bleeding. This reversal of the effects of heparin is achieved by treating the patient's blood with an anticoagulant-reversing substance (e.g., protamine) capable of neutralizing heparin or other anticoagulating substances.

To successfully maintain anticoagulation during a surgical procedure, and neutralize the heparin at the conclusion of surgery, it is highly desirable to be able to quickly and accurately determine the concentration of heparin in the patient's blood. Unfortunately, since the activity of heparin varies significantly from batch to batch, and from patient to patient, these determinations cannot be made simply on the basis of the amount of heparin administered. Protamine also varies in potency from batch to batch and from patient to patient. Furthermore, protamine itself can act as an anticoagulant. Thus, for optimal reversal of a given heparin action, it is essential to use only that amount of protamine that will directly neutralize the amount of active heparin in a particular patient's blood.

Such reversals of a heparin action are detected by dose-response tests which measure changes in blood clotting time in response to differing doses of anticoagulant in order to determine the correct dose of anticoagulant for a particular patient. Clotting time or activated clotting time tests are used to determine whether a patient's blood has achieved the desired level of anticoagulation. Heparin/protamine (anticoagulant/neutralizer) titration tests have been developed to provide accurate determinations of heparin (anticoagulant) levels. Such tests are based on measuring the time necessary for the blood to coagulate. Consequently, these titration tests measure coagulation time as an empirical measure of blood viscosity. These titration tests are accurate; but they have three major drawbacks. They require relatively long times to conduct, they require relatively large blood samples and they are subject to variable results and inaccuracies due to operator related variances. Consequently, various alternative methods and apparatus have been proposed to address these drawbacks.

By way of example only, U.S. Pat. No. 5,629,209 ("the '209 patent") discloses apparatus and methods for detecting changes in human blood viscosity through use of cartridges that, in conjunction with a test apparatus, are used to detect changes in blood viscosity. Heparinized blood is introduced into the cartridge through an injection port and fills the blood receiving/dispensing reservoir. The blood then moves from the reservoir through at least one conduit into at least one blood-receiving chamber where it is subjected to a viscosity test. In this test, a freely movable ferromagnetic object is placed within the blood-receiving chamber. The ferromagnetic object is moved up and down by an electromagnet in the test apparatus. Changes in the viscosity of the blood through which the ferromagnetic object falls are detected by determining the position of the ferromagnetic object in the blood-receiving chamber over a given time period or a given number of rises and falls of the ferromagnetic object. The incoming blood sample can be mixed with a blood viscosity altering agent (e.g., protamine) as it passes through the conduit to the blood-receiving chamber. Any air in the fluid communication system in front of the incoming blood sample is vented through an air vent/fluid plug device.

Applicants are co-inventors in the '209 patent and regard it as the closest prior art to the present invention. Therefore, its teachings are hereby fully incorporated into the present patent disclosure. The apparatus and methods described in the '209 patent are concerned with the same general issues e.g., test accuracy, test speed and operator safety that are further addressed in the present patent disclosure. Applicants' continued concern for these issues follows from the fact that the apparatus and methods of the '209 patent proved to have various drawbacks. These drawbacks have been eliminated or greatly diminished by the present invention. Many of these drawbacks were ultimately traced to the fact that a blood sample and the reagents (e.g., protamine) mixed into that blood sample by the apparatus and methods of the '209 patent were not uniformly mixed. This lack of uniformity of mixture resulted in test readings that sometimes proved to be unreliable. It would therefore be desirable to continue to employ, and enhance, the advantages originally brought about by the apparatus and methods taught in the '209 patent, while improving upon the reliability of the tests in which they are used. It also would be desirable to use these improvements in conducting other tests (e.g., those based upon changes in translucence, color, electrical conductivity, optical density, component concentration, electromotive response, etc.) on liquids other than human blood.

SUMMARY OF THE INVENTION

As was the case with the apparatus and methods of the '209 patent, the present invention is carried out through use of a disposable cartridge containing one or more simple testing chambers. This use of multiple chambers allows several tests to be performed simultaneously using uniform samples in a single cartridge. Thus, a second, third, etc. test carried out in that single cartridge can be a duplication of another test (to ensure greater reliability), or two or more entirely different tests can be conducted simultaneously. Here again, the amount of fluid contained within each test chamber is automatically determined. Hence, it will not vary from chamber to chamber or from test to test. The disposable cartridges of the present invention also are relatively small in size (thereby reducing the amount of storage space needed) and, likewise, relatively easy and inexpensive to manufacture.

The apparatus and methods of the present patent disclosure can be used in virtually any test where a reagent is mixed with a liquid sample and then tested for some change in a property of the resulting liquid/reagent mixture. The present apparatus and methods are particularly well suited for clotting time tests, dose-response tests, and especially titration tests on human blood taken from patients undergoing anticoagulation therapy during heart/lung bypass surgery. The apparatus and methods of the present invention are, however, much better able to detect changes in a property of a liquid relative to the results obtained with the apparatus and methods taught by the '209 patent. This improved accuracy also serves to expand the possible uses of the cartridges of the present invention to test where blood is not the liquid being tested. The basis for these improved test results will be discussed hereinafter in far greater detail.

A test procedure of the present patent disclosure commences when a liquid sample to be tested is introduced, under pressure, into a cartridge made according to the teachings of this patent disclosure. The cartridge can be loaded with a liquid sample when the cartridge is outside of the test machine or after the cartridge is inserted in said machine. It is generally preferred to load the cartridge after it is placed in the test machine. The fluid injection can be done manually or automatically through an injection port in said cartridge. Loading the cartridge by means of a syringe is a preferred method of introducing a liquid such as a blood sample into the cartridge.

In any case, the pressured liquid to be tested by the present apparatus first flows into a fluid receiving/dispensing reservoir contained within the body of the present cartridge. From the fluid receiving/dispensing reservoir the pressured fluid moves through a conduit leading to a fluid-receiving chamber. The cartridge can have as few as one fluid-receiving chamber. It is preferred, however, that the fluid receiving/dispensing reservoir is provided with one or more (preferably from two to twelve and most preferably from four to six) separate conduits that each lead to a respective fluid-receiving chamber. Such a reservoir/conduit/fluid-receiving chamber fluid communication system enables all the chambers to be filled more or less simultaneously. In some of the more preferred embodiments of this invention, the fluid communication between the fluid receiving/dispensing reservoir and the fluid-receiving chamber(s) is via a conduit having a constricted passage. As was the case in the cartridges of the '209 patent, each fluid-receiving chamber is further provided with an air vent/fluid plug device that is in fluid communication with a given fluid-receiving chamber. Thus, any air contained within the reservoir, conduit, and fluid-receiving chamber is driven before the incoming liquid and vented through one or more of these air vent/fluid plug device(s) as fluid enters and passes through the system. Again the air vent/fluid plug device, although porous to air, is non-porous to a liquid; thus, when the liquid sample reaches a given air vent/fluid plug device, it establishes a liquid lock and thereby prevents further movement of the liquid i.e., out of the cartridge via a given vent/fluid plug.

The fluid (air plus liquid) flow paths from the receiving/dispensing reservoir, through a given conduit and into a given fluid receiving chamber in the cartridge of the present invention do however differ from the analogous path(s) described in the '209 patent. At first glance, these differences may not appear to be radical or extensive. Nonetheless, applicants have found that their use has a very significant effect on the reliability of test results produced by use of the cartridges of this patent disclosure vis-à-vis the results produced by the cartridges described in the '209 patent.

There are at least three physical differences between the cartridges taught in the '209 patent and the cartridges of the present invention. Applicants have found that each of these three differences serves, in its own right, to improve upon the test results produced by the cartridges taught in the '209 patent. The combined use of 2 or 3 of these differences produces incrementally better and better results with each added feature. The first physical difference between the '209 cartridges and the cartridges of the present patent disclosure is the fact that the conduits located between the fluid receiving/dispensing chamber and a given fluid-receiving chamber in the present invention are provided with a constricted passage section. This constricted passage section is located between a given fluid-receiving chamber and the remainder of the conduit that feeds into the given fluid-receiving chamber from the fluid receiving/dispensing chamber. In the more preferred embodiments of this invention, the constricted passage will have a cross sectional area that is from about 20 to about 80 percent of the cross sectional area of the conduit that feeds fluid into that constricted passage. Preferably the conduits of the present cartridges will have cross sectional areas of from about one square millimeter (1 mil$^2$) to about three square millimeters (3 mil$^2$). Constricted passages having cross sectional areas of from about 20 to about 50 percent of that of its feed conduit are even more preferred. Such a constricted passage (owing to principles associated with Bernoulli's law) serves to increase the velocity of fluid flow through said constricted passage. Applicants have found that this increase in fluid velocity serves to significantly increase the degree of mixing between a liquid and any reagent mixed into that liquid.

The reagent can be mixed with the liquid before said liquid enters the cartridge, or the reagent be positioned in the conduit such that it comes into contact with the incoming liquid before the resulting liquid/reagent mixture enters the constricted passage. In some of the more preferred embodiments of this invention, however, the reagent is placed in the constricted passage itself. Under any of these liquid/reagent mixing circumstances, the increase in liquid velocity in the restricted passage serves to mix the reagent with the liquid much more thoroughly than the system taught in the '209 patent wherein the conduit between the fluid receiving/dispensing reservoir and the fluid-receiving chamber has no such constricted passage.

The second physical difference between the cartridges taught in the '209 patent and those employed in the present invention is the fact that the fluids introduced into the fluid-receiving chamber(s) of the present invention are introduced into said chamber(s) in a substantially tangential flow pattern. That is to say that the incoming fluid flow is not directed at the center of a fluid-receiving chamber, as it is under the teachings of the '209 patent (see for example FIG.

9 of said '209 patent), but rather is directed more toward the periphery of said fluid-receiving chamber. For the purposes of this patent disclosure, the expression "substantially tangential flow pattern" can be taken to mean that the incoming flow is aimed at a point in the fluid-receiving chamber that is more than about half way beyond the center of the fluid-receiving chamber in a direction toward an outer wall of said fluid-receiving chamber. In some more preferred embodiments of this invention, the incoming fluid flow will be directed in a path that is substantially tangent to a fluid-receiving chamber wall that is round in configuration. In other preferred embodiments of this invention, this tangential flow also will be directed into an upper portion of the fluid-receiving chamber e.g., near its roof region as opposed to its base region (see for example, FIG. 14). In yet another preferred embodiment of this invention, the incoming fluid flow will enter a given fluid-receiving chamber by an entry port that is elliptical in shape (as opposed to the round entry ports implicit in the '209 patent).

The third physical difference between the cartridges of this patent disclosure and those taught in the '209 patent is that the air vent/fluid plug device of the present invention is placed in fluid communication with the fluid-receiving chamber by means of a fluid exit conduit that is mounted in a substantially tangent manner with respect to a wall of said fluid-receiving chamber. That is to say that fluid flow out of the fluid-receiving chamber via the fluid exit conduit takes place at an angle that is substantially tangent to an external wall of the fluid-receiving chamber rather than substantially perpendicular to that external wall. Applicants have found that this fluid exit arrangement better serves to purge air from the fluid-receiving chamber as incoming liquid fills said fluid-receiving chamber. In other preferred embodiments of this invention, this exiting tangential flow also will be directed out of an upper portion of the fluid-receiving chamber (near its roof region, as opposed to its base region) and into an upper region of a vent/fluid plug device (near its roof region) as opposed to a base region of said vent/fluid plug device (see generally FIG. 14). In yet another preferred embodiment of this invention, the exiting fluid flow will leave a fluid-receiving chamber by an exit port that also is elliptical in shape (again, as opposed to the round shapes implicit for these comparable chamber exit ports in the '209 patent). In still other preferred embodiments of this invention, the fluid exit port leading from a fluid-receiving chamber to a vent/fluid plug device will be substantially opposite to the position of the fluid entry port leading into said fluid-receiving chamber.

Again, applicants have found that each of the above noted fluid flow features, in its own right, will help a given test apparatus produce more accurate test results. Of these three differences between the cartridges of the present invention and those of the '209 patent, use of a constricted passage is the somewhat more influential. In any case, use of two of these fluid flow related features (e.g., (1) constricted passage plus tangential flow into chamber, (2) constricted passage plus tangential flow out of chamber, (3) tangential flow into and out of chamber, etc.) will produce better results than use of just one of them. In the same vein, use of all three of these fluid flow features will produce still better test results.

Moreover, these cumulative improvements appear to be the case, regardless of the nature of the liquid being tested, regardless of the nature of the reagent mixed with the liquid in the test cartridges of this patent disclosure and regardless of the type test performed on a liquid/reagent mixture in the fluid-receiving chamber. Thus, the cartridges of this patent disclosure can be used in virtually any test wherein changes in a property of a liquid/reagent mixture is to be measured e.g., changes in viscosity, translucence, color, electrical conductivity, optical density, fluid component concentration, electromagnetic response and so on. Thus, even though a biological fluid (i.e., blood) is used as the primary example in this patent disclosure, other fluids that must be mixed with a reagent in order to perform a test (e.g., other "biological" fluids such as urine, DNA suspensions, as well as "non-biological" fluids, e.g., industrial chemical compositions, laboratory chemical compositions) can be tested using the hereindescribed cartridge features, geometries and test procedures.

Another physical difference between the cartridge devices taught by the '209 patent and those of the present patent disclosure is primarily concerned with better (e.g., safer, simpler, etc.) handling procedures (as opposed to better sample mixing procedures) for the cartridge, especially when it is inserted into, and removed from, the machine in which a test is performed. In the case of the present invention, a syringe used to inject a fluid sample into a cartridge can also serve as a "handle" for the cartridge, thereby eliminating the need for the operator to touch the cartridge with his (her) hands. This less than desirable circumstance was implicit in the use of the cartridges taught in the '209 patent. Under the teachings and methods of the present patent disclosure, the syringe handle and cartridge are preferably inserted into the test machine and thereafter disposed of as a single unit. Thus, this difference (the use of a syringe as a "handle" for the cartridge) does not effect test results, but rather improves upon the ease and safety associated with loading and unloading the present cartridges into and out of a given test machine. To this end, the fluid receiving/dispensing reservoir of the cartridge receives the subject fluid through an injection port/syringe connector that leads from the top side of the cartridge near its rear end. Preferably an injection port/syringe connector is attached to the cartridge at an upwardly directed angle. Thus, when a syringe is connected to the injection port/syringe connector, the syringe serves as a handle for inserting the attached cartridge into the test machine and, upon completion of the test, taking said cartridge back out the machine. Again, the syringe/handle and the cartridge are most preferably disposed of in this assembled or unified state. Thus, the test machine operator is better protected from contact with the fluid being tested relative to the human finger operated insertion method suggested in the '209 patent.

To these ends, the nose of a syringe can be designed to be tightly compression fitted into the cartridge's injection port in order to maintain this assembled state. In yet another preferred embodiment of this invention, the injection port and the nose of the syringe will be provided with an interlocking device such as a threading systems or so-called "bayonet" locking device whose operation involves inserting a nub or other projection on one element (e.g., the nose of the syringe) into a keyway having a laterally positioned projection receiver. Thus, the nub (or other projection) is forced into the projection receiver by rotating the fully inserted syringe about 90° in the cartridge injection port. These and other advantages, features, and objects of the present invention will be more readily understood in view of the following more detailed descriptions and the drawings.

BRIEF DESCRIPTION OF THE DRAWINGS

FIG. 4 is a side view of the cartridge shown in FIG. 2.

FIG. 5 is a side view of the cartridge shown in FIG. 2 with a syringe attached to said cartridge.

FIG. 11 is a top view of another cartridge made according to the teachings of this patent disclosure.

FIG. 12 is a rear view of the cartridge shown in FIG. 11.

FIG. 13 is a bottom view of the cartridge shown in FIG. 11.

FIG. 14 is an enlarged, cut-away, cross-sectional view of the cartridge shown in FIG. 11 being used in conjunction with a syringe.

DETAILED DESCRIPTION OF PREFERRED EMBODIMENTS

Figure 1:
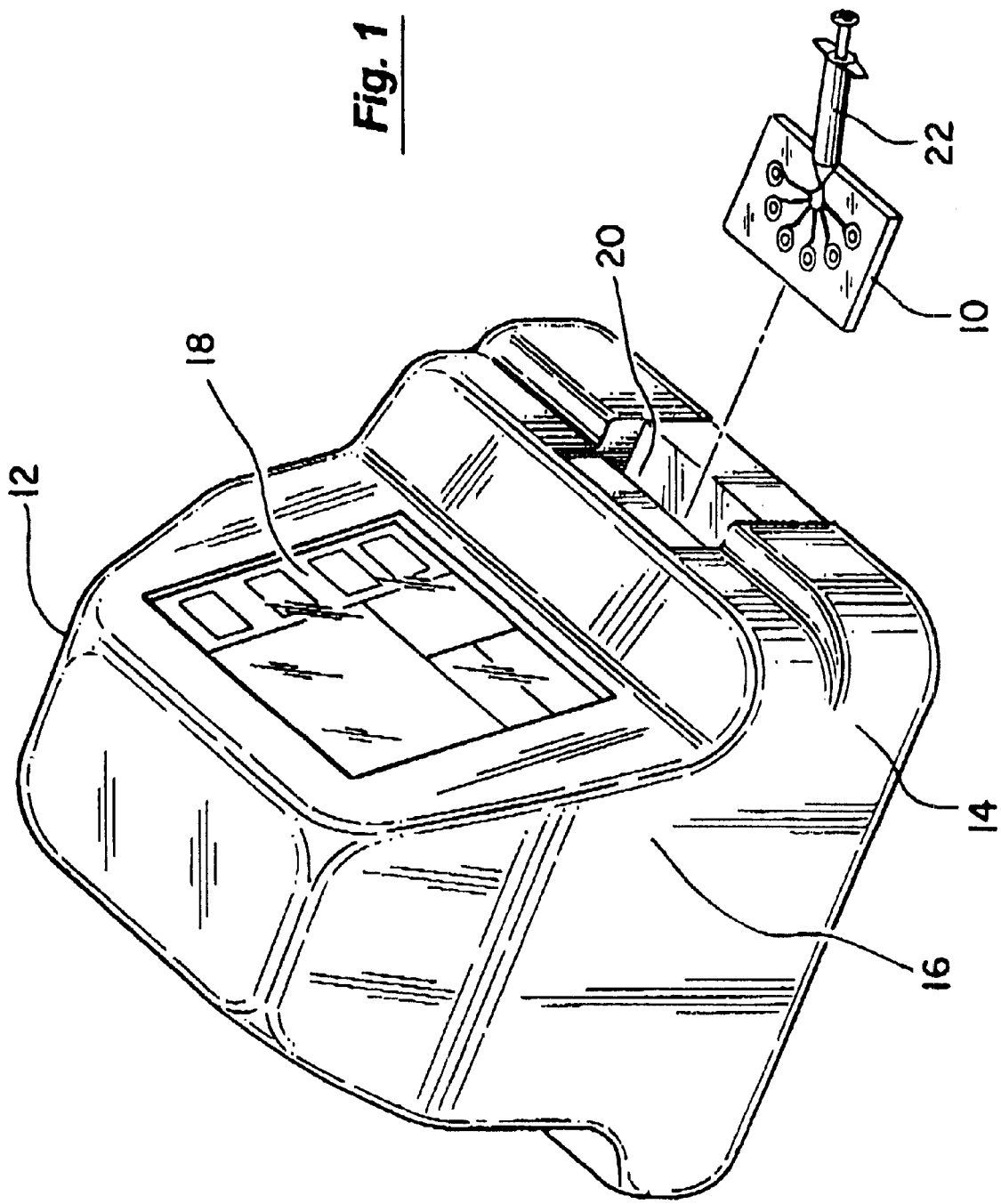
FIG. 1 is a perspective view of a cartridge and a test machine in which the cartridge is inserted.

FIG. 1 depicts a disposable cartridge 10 conceptually associated with a machine 12 for testing some property of a liquid that is mixed with a reagent. The machine 12 can be provided with one or more sensor devices (known to those skilled in the test machine manufacturing arts), for detecting various properties of a given liquid/reagent sample. For example, the one or more sensing devices can be used to detect the viscosity, translucence, color, optical density, electrical conductivity, magnetic properties, fluid component concentrations, electromagnetic response, etc. of a sample (or an object placed in the sample e.g., the ferromagnetic washer shown in FIGS. 9, 10 and 14). That is to say that in some of the more preferred embodiments of this invention, the machine 12 will be provided with more than one kind of sensing devices so that the machine 12 can simultaneously (or sequentially) detect more than one property of the sample being tested. Such a machine 12 will generally comprises a base 14 and an upper portion 16. The upper portion 16 preferably includes a display device 18 (including a touch-sensitive display screen) such as that depicted in FIG. 1. Contained within the base 14 of the machine 12 is a cartridge holder mechanism (not shown). The cartridge 10 is inserted into the cartridge holder mechanism via a slot 20 that is preferably located in the front of the base 14.

Be the nature of the test(s) as it (they) may, the cartridge 10 may be inserted into the machine 12 before or after said cartridge 10 is filled with a liquid sample to be tested. FIG. 1 also depicts a particularly preferred embodiment of this invention wherein a syringe 22 is used to fill the cartridge 10 with a liquid to be tested. In the more preferred embodiments of this invention, the syringe 22 is used to fill the cartridge 10 with the liquid sample after the cartridge is inserted into the slot 20 in the base 14. Thereafter, the syringe 22 remains attached to the cartridge 10 in the manner suggested in FIG. 1. So attached, the syringe 22 can conveniently serve as a "handle" for the cartridge 10. This syringe/handle feature is very useful in performing the manual operations associated with placing the cartridge 10 in the cartridge receiving slot 20 and subsequently removing the cartridge 10 from said slot. The cartridge and its syringe/handle are preferably disposed of as a unit. This feature serves to protect the machine operator from inadvertent contact with the liquid being tested.

After a cartridge 10 containing a liquid sample is placed in the slot 20, the machine 12 conducts an analytical test following some predetermined procedure in accordance with the type of test desired. Such procedures are known to those skilled in the manufacture of test machines. These test results also may be compared (for example, through computer-programmed comparisons) with other programmed test information and/or with other test results. For example, the detailed test procedures taught in the '209 patent can be carried out. Again, the machine 12 will preferably display the results of the test on a display screen 18.

Figure 2:
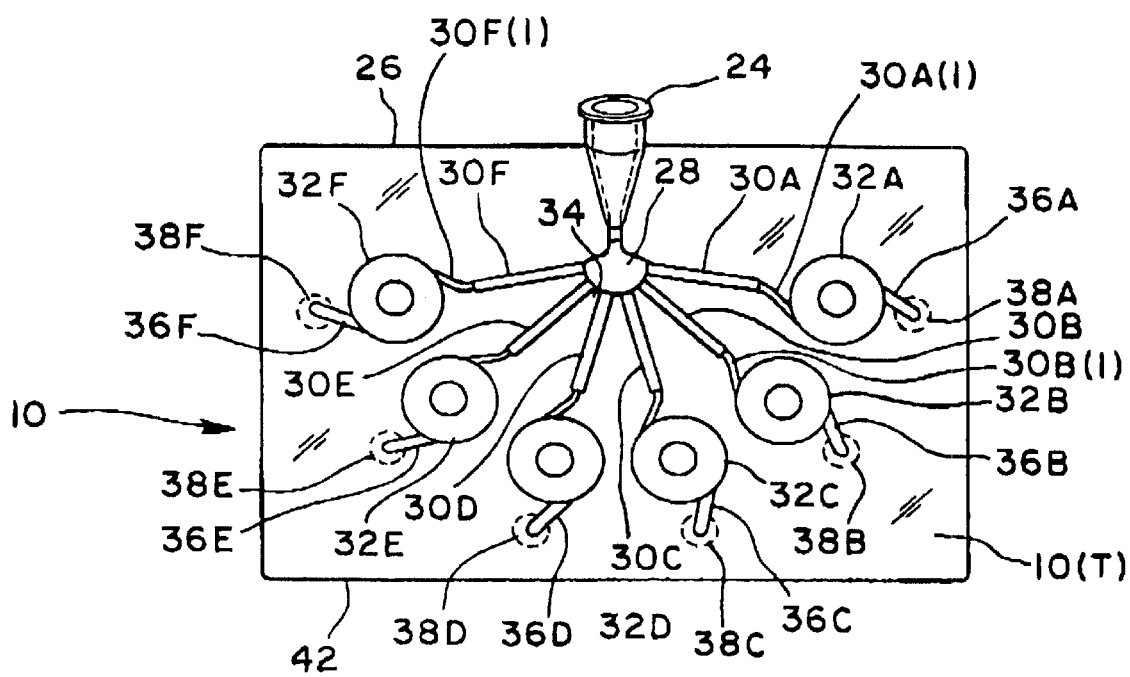
FIG. 2 is a top view of a cartridge made according to certain preferred embodiments of this invention.

FIG. 2 shows a top view of a preferred embodiment of a cartridge 10 such as that depicted in FIG. 1. The cartridge 10 is substantially planar and formed of a strong, rigid material (for example, a plastic or acrylic) that is, most preferably, inert with respect to the liquid/reagent sample being tested. The rigid material from which the cartridge 10 is formed may be partially or wholly transparent. The cartridge 10 may be manufactured as a unitary or monolithic piece (for example, by injection molding techniques), or it may be assembled from various separate parts. In one particularly preferred manufacturing method (see FIG. 3), a separate and distinct cartridge top 10(T) is attached on a cartridge bottom 10(B) after a liquid sample altering reagent (e.g., a blood viscosity-altering reagent) is placed in a conduit (e.g., conduit 30A) in the cartridge bottom 10(B). In some particularly preferred embodiments of this invention, the cartridge top 10(T) will be a flexible material that is used to cover the top of the fluid communication system and thereby form the top of the cartridge. This flexible material is preferably a polymer based, paper based material. In either case the material should be impervious to the liquid sample. In some of the more preferred embodiments of this invention this flexible material will have a label-like quality in that select portions of its underside are provided with an adhesive material. The top side of this label could have printed material such as directions for using the cartridge, bar codes, words of caution, and/or technical specifications, etc. In other preferred embodiments of this invention, the top of the cartridge will be a stiff, transparent, plastic material such as Mylar®. It is to be understood, however, that various other types of plastic materials may be used for such tops 10(T) so long as they provide a fluid-impervious seal between the top 10(T) and the cartridge bottom 10(B). The cartridge bottom 10(B) is preferably made of compatible plastic materials that are capable of being held in an abutting relationship by a glue or adhesive material.

As shown in FIG. 2, the cartridge 10 is provided with an injection port 24 that is located in a nominal rear portion 26 of the cartridge 10. A liquid sample is introduced into the cartridge 10 through this injection port 24. The injected liquid may already have been mixed with a reagent before it enters the cartridge. In certain more preferred embodiment of this invention, however, the mixing of the liquid and reagent takes place inside the cartridge 10. In any case, the injection port 24 directs the liquid sample into a fluid receiving/dispensing reservoir 28. From the fluid receiving/dispensing reservoir 28, the liquid sample proceeds through one or more fluid inlet conduits 30A, 30B, 30C . . . 30F, etc. Each such conduit respectively leads to a fluid-receiving chamber 32A, 32B, 32C . . . 32F, etc. The motive force for this movement of the subject liquid (e.g., blood) through the cartridge 10 is provided by a fluid injection or pumping mechanism. A manually operated syringe such as the syringe 22 shown in FIG. 1 is a preferred means (but not the only means) for pumping the liquid sample through the cartridge 10. In some of the more preferred embodiments of this invention the conduits 30A, 30B . . . 30F are provided with a constricted portions 30A(1), 30B(1) . . . 30F(1) that angle from a direction that generally leads toward the center of the respective fluid-receiving chambers 32A, 32B . . . 32F, to their respective wall regions.

Most preferably, each fluid-receiving chamber 32A, 32B, 32C, etc. is equidistant from the fluid receiving/dispensing reservoir 28. Consequently the liquid sample moves from the fluid receiving/dispensing reservoir 28 simultaneously, or nearly so, into each fluid-receiving chamber 32A, 32B, 32C, etc. In those embodiments of this invention in which the liquid sample being tested is human blood, each fluid-receiving chamber 32A, 32B, 32C, etc. will preferably have a volume of about 100 μl to about 250 μl. Although six fluid-receiving chambers 32A, 32B, 32C, etc. are shown in FIG. 2, it should be understood that any desired number of fluid-receiving chambers can be formed in the cartridge 10. Indeed, applicants' cartridges could contain only one such fluid-receiving chamber.

Figure 3:
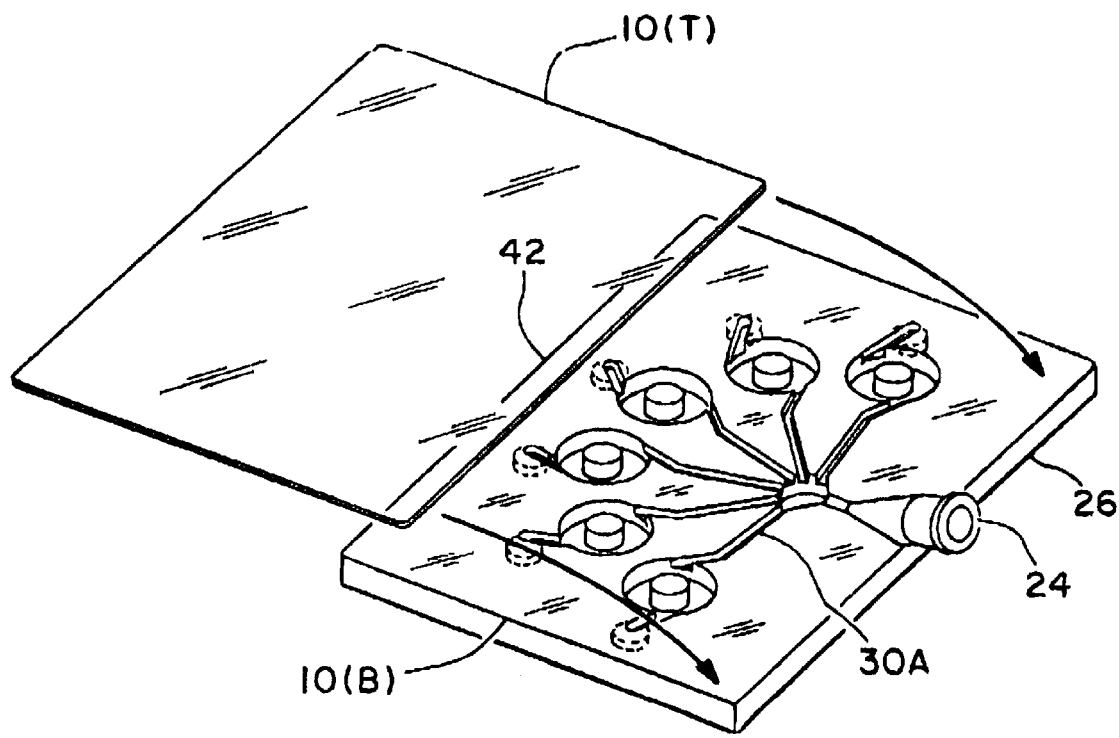
FIG. 3 is a perspective, exploded, view of the cartridge shown in FIG. 2.

Again, however in the more preferred embodiments of this invention, multiple fluid-receiving chambers 32A, 32B, 32C, etc. preferably will be filled nearly simultaneously in order to enhance the accuracy of the analytical test results. To achieve this near-simultaneous filling, the fluid receiving/dispensing reservoir 28 is preferably provided with a substantially semicircular configuration so that, upon being filled, it acts as a manifold that tends to uniformly deliver the liquid sample to the fluid-receiving chambers 32A, 32B, 32C, etc. As seen in FIGS. 3, 4 and 5, the injection port 24 most preferably enters the top 10(T) and rear 26 of the cartridge 10. It is then pressured (e.g., by a syringe) into the fluid receiving/dispensing reservoir 28. As can be better seen in FIG. 14, the conduits 30A, 30B, 30C, etc. preferably are arrayed along the front end 34 of the fluid receiving/dispensing reservoir 28. The conduits 30A, 30B, 30C, etc. most preferably are located closer to the top of the fluid receiving/dispensing reservoir 28 relative to location of the fluid inlet leading into the fluid receiving/dispensing chamber 28 from the injection port 24. Thus, a fluid sample preferably enters a lower part of one end of the fluid receiving/dispensing reservoir 28, substantially fills the fluid receiving/dispensing reservoir 28 and then leaves said chamber 28 at a relatively higher level of the fluid receiving/dispensing reservoir 28.

Any air contained in the cartridge 10 must be vented as the liquid sample is pumped into said cartridge. To this end, each fluid receiving chamber 32A, 32B, 32C, etc. is provided with a second conduit 36A, 36B, 36C, etc. ("fluid exit conduits") that lead from a given fluid-receiving chamber 32A, 32B, 32C, etc. to a given air vent/fluid plug device 38A, 38B, 38C, etc. Such a vent/fluid plug is detailed in FIGS. 9 and 10. As the liquid sample enters the cartridge 10 and moves into the fluid receiving/dispensing chamber 28, air contained in the conduits 30A, 30B, 30C, etc., the fluid receiving/dispensing reservoir 28, fluid-receiving chambers 32A, 32B, 32C, etc., the fluid exit conduits 36A, 36B, 36C, etc. and the vent/fluid plug devices 38A, 38B, 38C, etc. is driven before the incoming fluid and vented out of the cartridge 10. Most preferably this venting will be done through the bottom side 40 of the cartridge 10 (see FIGS. 13 and 14) via air vent/fluid plug device 38. This venting also could be done through the top 10(T) or side(s) 42 of the cartridge 10 as well. The exit conduits 36A, 36B, 36C, etc. preferably exit their respective fluid receiving chambers 32A, 32B, etc. at a position that is substantially opposite the position where the fluid inlet conduits 30A, 30B, etc. enter their respective fluid-receiving chambers 32A, 32B, etc.

When the incoming liquid reaches the air vent/fluid plug device 38, a permanent liquid lock is formed. This prevents any further motion of liquid through the cartridge 10. In other words, the air vent/fluid plug device 38 allows air displaced by incoming liquid to exit the cartridge 10, but prevents liquid from leaving the cartridge 10 via said air vent/fluid plug device 38. In one of the more preferred embodiments of this invention, the air vent/fluid plug device 38 is formed of Porex® plastic (Porex Corp. no. X6870). This material is porous to a gas such as air, but is not porous to a liquid such as blood, and therefore acts as a liquid lock. The fluid communication system created by the fluid receiving/dispensing reservoir 28, conduit(s) 30A, 30B, etc., fluid-receiving chamber(s) 32A, 32B, etc., and air vent/fluid plug device(s) 38A, 38B, etc. automatically places the correct amount of liquid in each fluid-receiving chamber 32A, 32B, etc. Hence, no liquid volume measurements need to be made by human operators. This automatic measuring action provides a means whereby the volume of the fluid samples will not vary between the respective fluid-receiving chambers 32, or between tests. Fail-safe provisions also may be provided by the machine 12 to disclose incomplete filling of any fluid-receiving chamber 32.

FIG. 3 is an exploded perspective view of the cartridge 10 shown in FIG. 3. In this disassembled state a reagent can be readily placed in one or more of the conduits (e.g., conduit 30A). In some particularly preferred embodiments of this invention, the reagent will be placed in conduit in the form of a solution or suspension. The carrier (water, alcohol, etc.) for the reagent will then be evaporated and thereby leaving behind a dried form of the reagent. The cartridge top 10(T) then can be placed on the cartridge bottom 10(B) e.g., by gluing, by an adhesive placed on the underside of a flexible, label-like cartridge top 10(T), and thereby form the unified cartridge 10 shown in FIGS. 1 and 2.

Figure 3A:
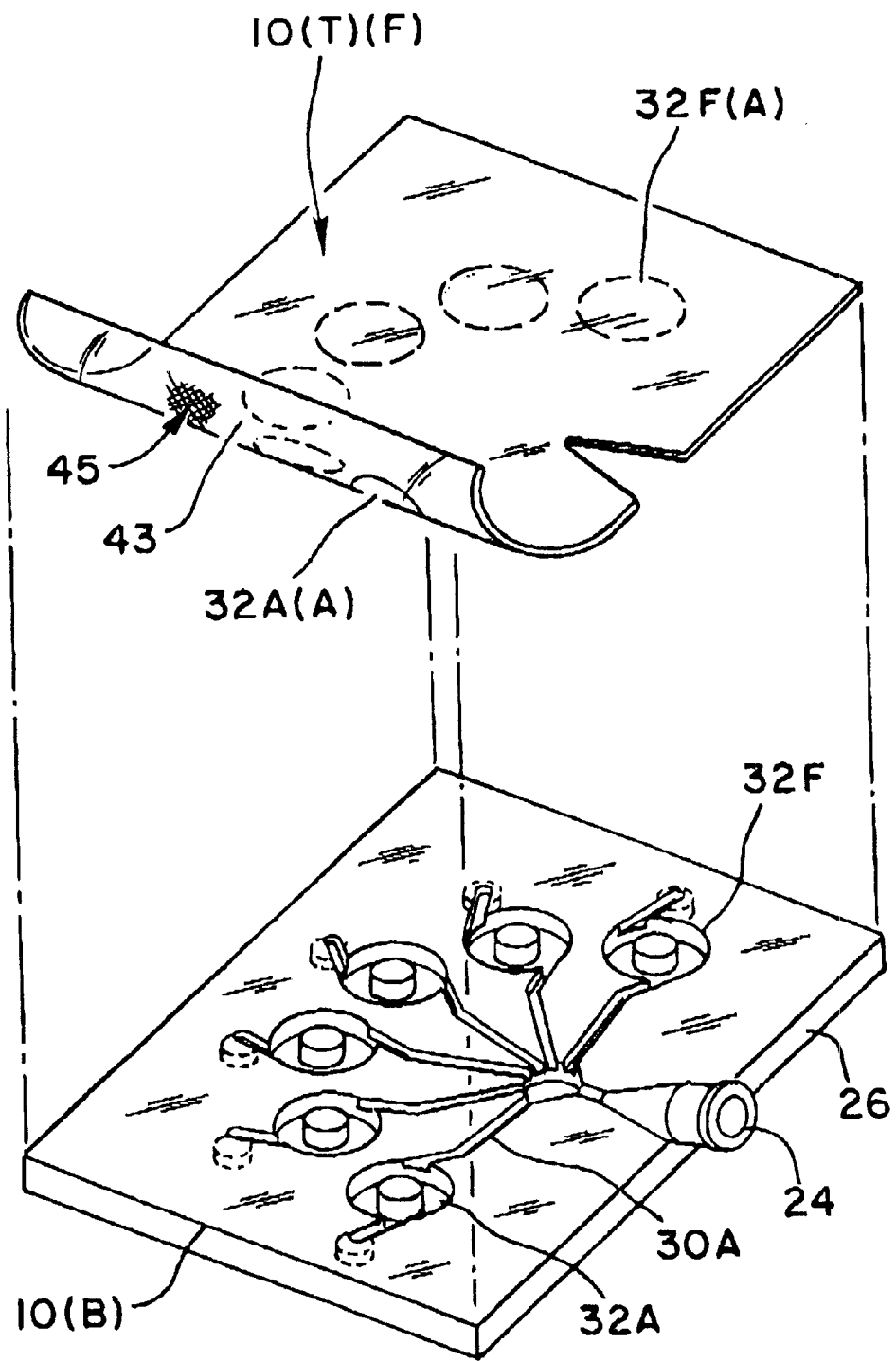
FIG. 3A is a perspective, exploded, view of the cartridge of FIG. 3 about to be provided with a flexible top 10(T)(F).

FIG. 3A is an alternative embodiment of this invention wherein a top 10(T)(F) for the cartridge bottom 10(B) is made of a flexible material whose left end is shown curled away from a flat configuration. The underside 43 of the top 10(T)(F) is provided with regions having an adhesive material 45. The adhesive material 45 is, most preferably absent from those areas that cover the fluid receiving chambers 32A . . . 32F, i.e., those round areas on the underside 43 of the top 10(T)(F) designated as 32A(A) . . . 32F(A).

FIG. 4 is a side view of the cartridge 10 shown in FIG. 2. It particularly illustrates how the injection port 24 is mounted to the top 10(T) and/or rear end 26 of the cartridge 10 at an angle beta. This angle beta will preferably be from about 30° to about 45°.

FIG. 5 is a partially cut away side view of the cartridge 10 shown in FIG. 2 having a syringe connected to the injection port 24. The syringe 22 can be used as a handle for the cartridge 10. This cut away view also suggests that a threaded nose 25 of the syringe can be threaded into a threaded injection port 24.

Figure 6:
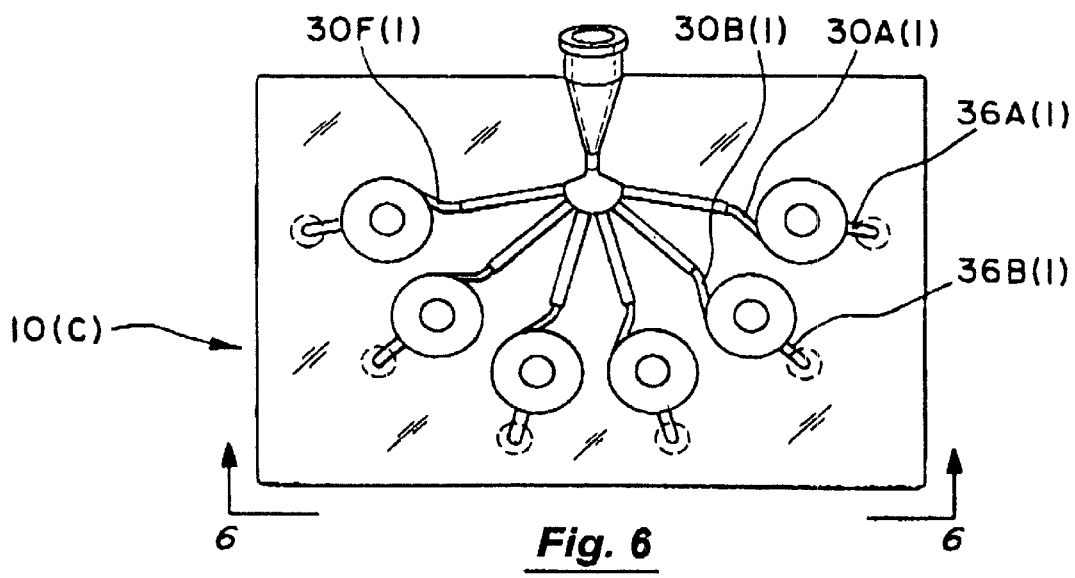
FIG. 6 is a top view of another embodiment of the cartridges of this patent disclosure.

FIG. 6 depicts another embodiment of this patent disclosure wherein a cartridge 10(C) is provided with six fluid receiving chambers. The fluid exit conduits (e.g., 36A(1), 36B(1), etc.) are in a less preferred, but still operable, orientation with respect to their fluid chambers. That is to say that these fluid exit conduits 36A(1), 36B(1), etc. are shown respectively directed at the center of said chambers rather than being tangent to them.

Figure 7:
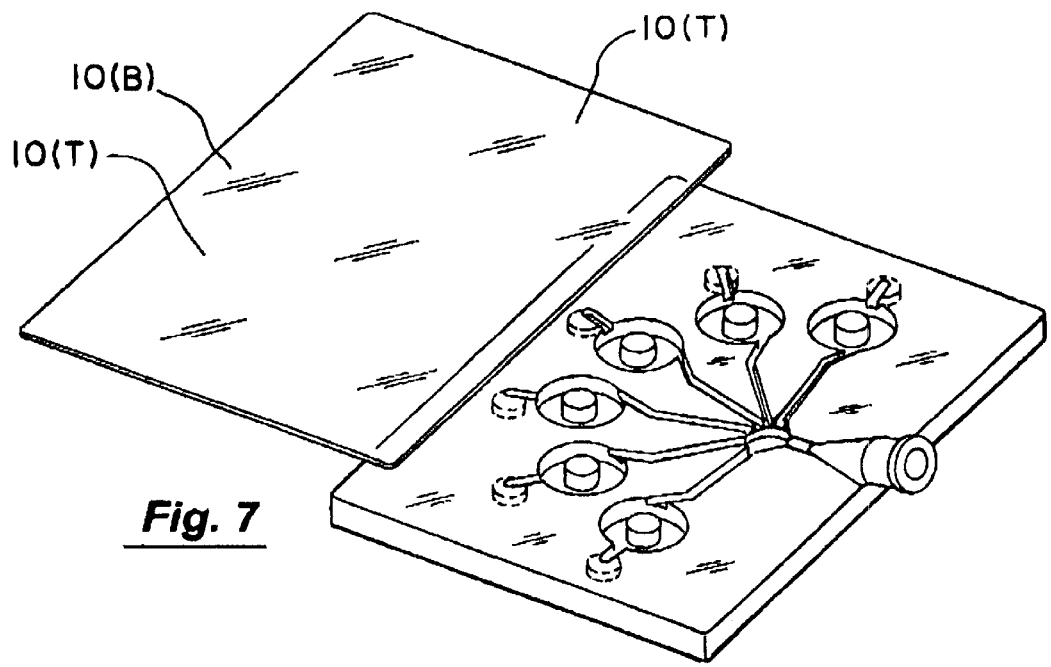
FIG. 7 is a perspective, exploded view of the cartridge shown in FIG. 6.

FIG. 7 is an exploded view of the cartridge shown in FIG. 6.

Figure 8:
FIG. 8 is a rear view of the cartridge shown in FIG. 6.

FIG. 8 is a rear view of the cartridge 10(A) shown in FIG. 6.

Figure 9:
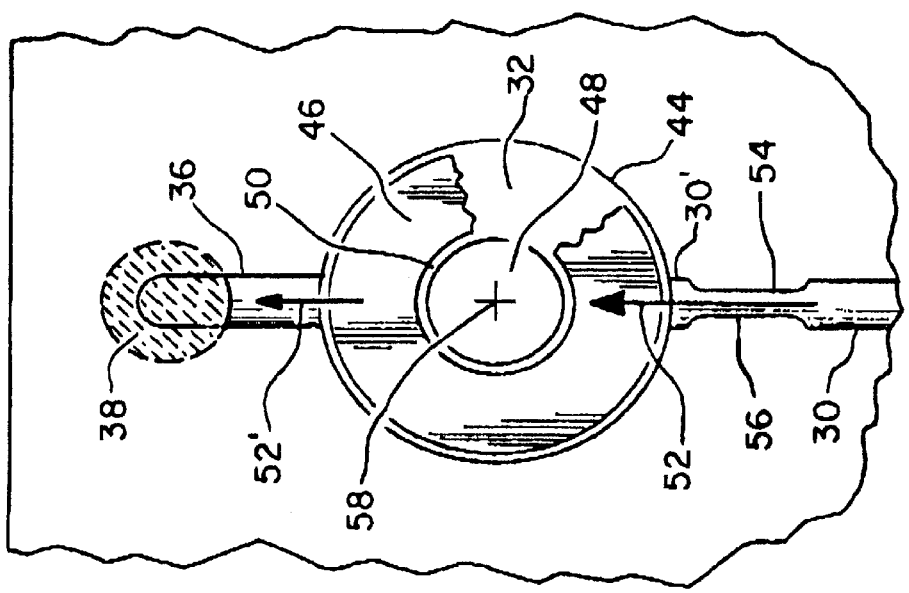
FIG. 9 is an enlarged top view of a fluid entry conduit, fluid-receiving chamber, fluid exit conduit and vent/fluid plug device of this patent disclosure.

FIG. 9 is an enlarged top view of a fluid-receiving chamber 32 and the fluid inlet conduit 30, fluid exit conduit 36 and air vent/fluid plug 38 associated with it. It also illustrates use of this invention in a test wherein: movement of a ferromagnetic washer-like object 46 is the means of detecting changes in a property of the sample (e.g., the viscosity of the blood sample). In such a test, at least one, and preferably each, fluid-receiving chamber will contain such a freely movable ferromagnetic object such as the washer-like object 46 depicted in FIGS. 9, 10 and 14. When a blood viscosity analysis is performed, the ferromagnetic object 46 is raised under a magnetic action to the top of the chamber and then is permitted to fall through the blood/reagent mixture to the bottom of the chamber. One or more characteristics of the descent of the washer (e.g., descent time) can measured by detecting the position of the ferromagnetic object under various conditions (e.g., after repeated raising and lowering of the washer). This reciprocating motion of the ferromagnetic object is repeated until a change in fall time in one or more of the fluid-receiving chambers signals a change in the viscosity of the blood/reagent mixture within those one or more fluid-receiving chambers. FIG. 9 also shows that the fluid-receiving chamber 32 preferably has a round external wall 44. As can be better seen in FIG. 14, the washer-like object 46 is free to vertically rise and fall inside the chamber 32. This vertical rise and fall may be guided by a center post 48 in the chamber. In effect a center post 48 may occupy the washer-like object's center hole 50.

FIG. 9 also depicts a fluid sample 52 being pumped into the fluid-receiving chamber 32 via conduit 30. The conduit 30 is shown provided with a constricted passage 54. A reagent 56 (e.g., a dried blood viscosity changing reagent) is shown positioned in a center region of said constricted passage 54. In this view, the constricted passage flares out into a conduit section 30' having a cross section comparable to the fluid inlet conduit 30 before leading into the fluid-receiving chamber 32. In FIG. 9, conduit 30 is shown positioned in a less preferred, but still operable, orientation with respect to the fluid-receiving chamber 32. That is to say that, in effect, the flow 52 of the fluid sample is aimed at the center 58 of the fluid-receiving chamber 32. Fluid flow 52' from the fluid-receiving chamber 32 exits said chamber, via fluid exit conduit 36, in a similar manner. That is to say that the exit flow 52' of the fluid is through an exit conduit 36 that is essentially perpendicular to the chamber wall 44 (i.e., the fluid flow 52' from the chamber 32 can be thought of as emanating from a region near the center 58 of said chamber). The exit conduit 36 leads to an air vent/fluid plug device 38.

Figure 10:
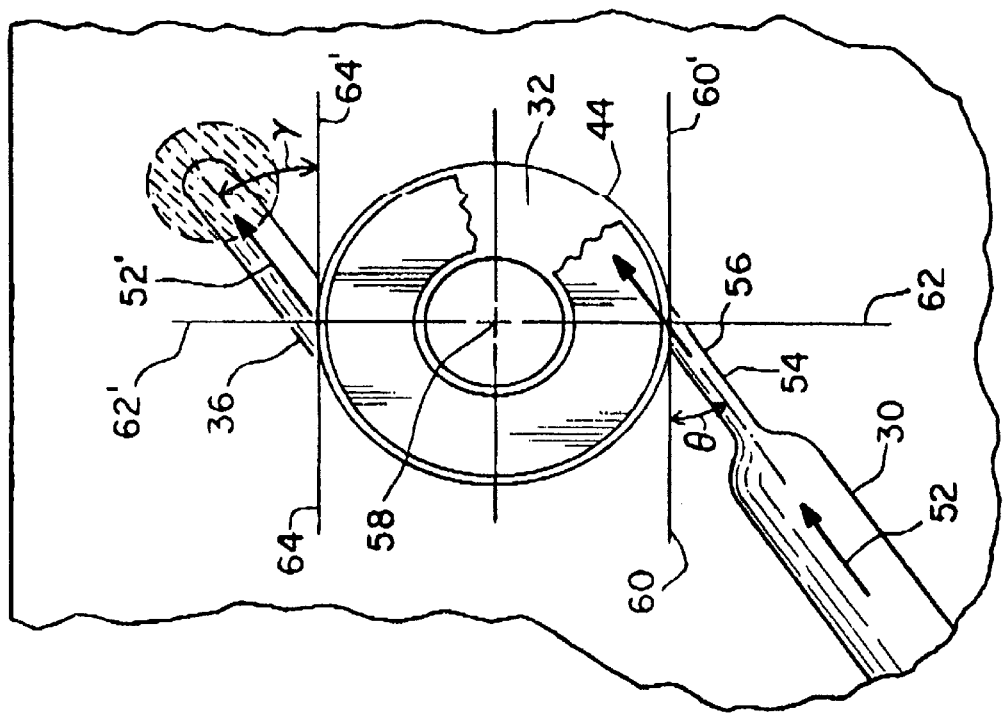
FIG. 10 is an enlarged top view of another fluid entry conduit, fluid-receiving chamber, fluid exit conduit and vent/fluid plug device of this patent disclosure.

FIG. 10 shows a particularly preferred embodiment of this invention wherein the inlet conduit 30 has a constricted passage 54 (containing a reagent 56) that leads into the fluid-receiving chamber 32 in a substantially tangential flow pattern. That is to say that the flow of fluid 52 into the fluid-receiving chamber 32 is directed more toward the outer wall 44 of the chamber rather than toward the chamber's center 58 (as it is in the embodiment shown in FIG. 9). This substantially tangential flow pattern is depicted in FIG. 10 by first placing a tangent line 60/60' on the chamber wall 44 such that it is substantially perpendicular to the round chamber's center line 62/62'. The angle theta at which the constricted passage 54 approaches the wall 44 of the fluid-receiving chamber 32 is preferably less than 45°. More preferably, the angle theta will be less than 20°; and most preferably this angle theta will approach the zero angle associated with tangent line 60/60'.

Figure 10A:
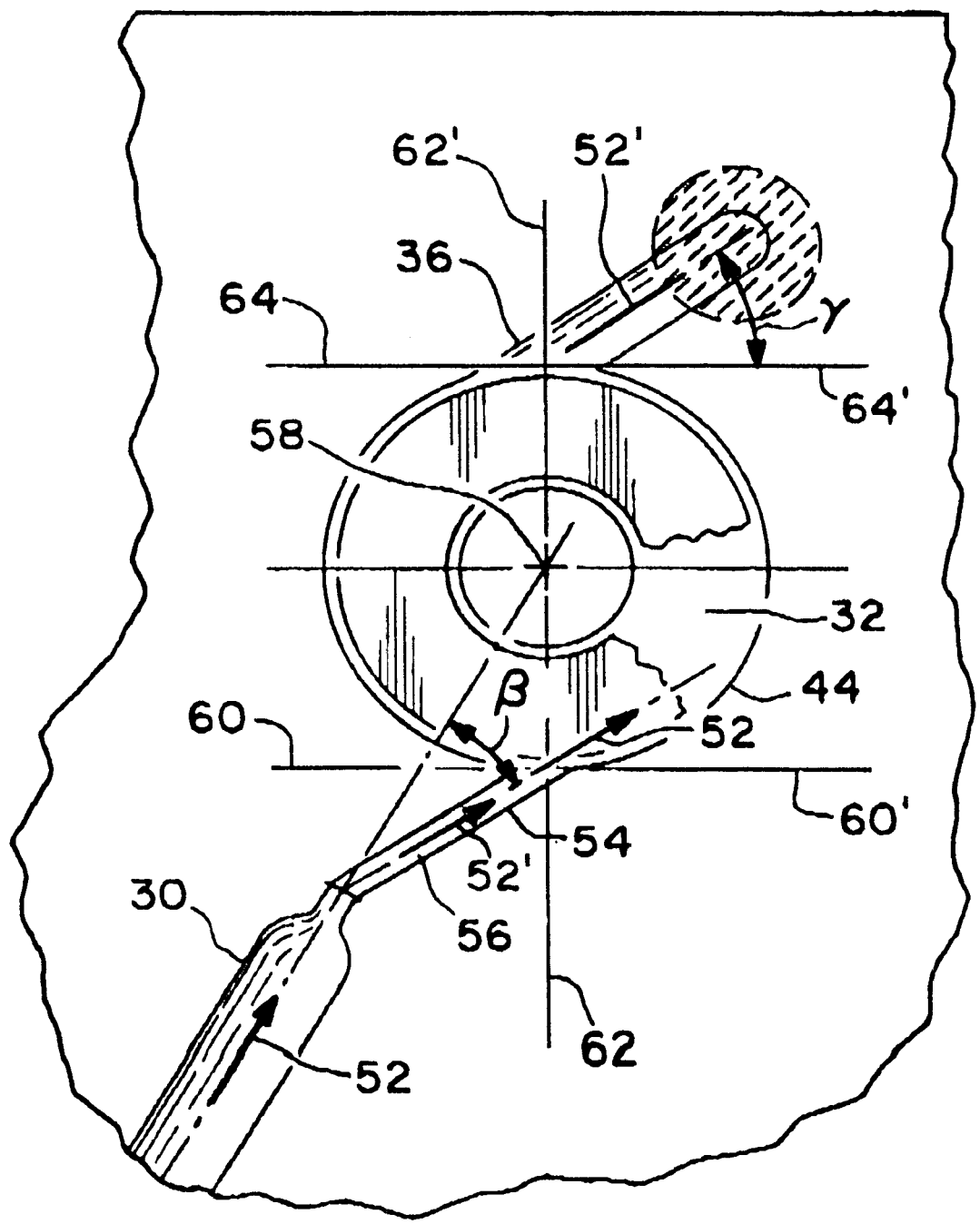
FIG. 10A is an enlarged top view of another cartridge made according to the teachings of this patent disclosure wherein the conduit between the fluid receiving/dispensing reservoir and the fluid-receiving chamber has a constricted region that angles from the first part of the conduit and approaches the wall of fluid-receiving chamber in a tangential manner.

FIG. 10A shows another particularly preferred embodiment of this invention wherein the inlet conduit 30 has a constricted passage 54 (containing a reagent 56) that leads into the fluid-receiving chamber 32 in a substantially tangential flow pattern. The flow 52 through a first portion of the conduit 30 is generally aimed toward the center 58 of the fluid-receiving chamber 32. This flow 52 is however directed into a constricted passage 54 at an angle Beta prime which is such that the flow 52 enters the fluid-receiving chamber 32 in a tangential fashion (as opposed to being aimed at the center 58 of the fluid-receiving chamber 32), near the perimeter or outer wall 44 of said chamber 32. That is to say that the flow of fluid 52 into the fluid-receiving chamber 32 is directed more toward the outer wall 44 of the chamber rather than toward the chamber's center 58 (as it is in the embodiment shown in FIG. 9). This substantially tangential flow pattern is depicted in FIG. 10A by first placing a tangent line 60/60' on the chamber wall 44 such that it is substantially perpendicular to the round chamber's center line 62/62'. The angle Beta prime at which the constricted passage 54 approaches the wall 44 of the fluid-receiving chamber 32 is preferably less than 45°. More preferably, the angle Beta prime will be less than 20°; and most preferably this angle Beta prime will approach the zero angle associated with tangent line 60/60'.

Similarly, fluid flow 52' out of the chamber 32 leaves in a tangential flow direction as well. This circumstance is depicted in FIG. 10A by virtue of the fact that the fluid flow 52' out of the chamber 32 follows a direction that does not pass through the center 58 of the chamber, but rather is more tangent to the round outer wall 44 of said chamber 32. This substantially tangential flow pattern is depicted in FIG. 10A by placing a tangent line 64/64' on the chamber wall 44 such that it is substantially perpendicular to the chamber's center line 62/62'. The angle gamma at which the exit conduit 36 leaves the wall 44 of the fluid-receiving chamber 32 is preferably less than 45°. More preferably, the angle gamma will be less than 20°; and most preferably this angle gamma will approach the zero angle associated with the tangent line 64/64'.

FIG. 11 shows a top view of another cartridge 10(B) constructed according to the teachings of this patent disclosure. In this embodiment, the inlet conduits 30A, 30B, 30C . . . 30F are each respectively aimed at a center of a fluid-receiving chamber 32A, 32B, 32C, etc. while the exit conduits 36A, 36B, 36C, etc. leave said chambers in a tangential direction.

FIG. 12 is an end view of the cartridge 10(B) shown in FIG. 11. It particularly illustrates a preferred embodiment of this invention when such a cartridge is made in two layers 10(B) and 10(T).

FIG. 13 is a bottom view of the cartridge 10(B) shown in FIG. 11. It illustrates an embodiment wherein the air vent/fluid plug devices 38 lead to the bottom side 40 of the cartridge 10(B).

FIG. 14 is an enlarged cross sectional view of the cartridge 10(B) shown in FIG. 11 as seen along section line 14—14 thereof. A syringe 22 is depicted as being threaded into an injection port 24 in the cartridge 10(B). It could be compression fitted as well. Such a compression fit also could be augmented by use of a locking device that mechanically connects the syringe 22 to the injection port 24. For example, the locking device may be a so-called "bayonet lock" wherein a nub or other protrusion on the syringe 22 may be guided into a first keyway. Upon reaching the bottom end of such a first keyway, the syringe 22 is rotated (about 90°) and thereby forcing the protrusion into a second receiver slot or keyway that is substantially perpendicular to the path of the first keyway.

Fluid flow 52 from the syringe 22 enters the injection port 24 and flows under pressure provided by the syringe 22 to the fluid receiving/dispensing chamber 28. Preferably, the fluid flow 52 will enter said chamber 28 at a level that is lower than the level at which fluid leaves said chamber 28 (i.e., at the level of conduit 30A). Fluid leaving chamber 28 enters inlet conduit 30A and flows to a fluid-receiving chamber 32. In one particularly preferred embodiment of this invention, the inlet conduit 30A has a constricted passage 54 (see again FIG. 10). In a particularly preferred embodiment of this invention the reagent 56 that the liquid will be mixed with is positioned in this constricted passage 54. Dried deposits of such reagents 56 are particularly preferred in this particular location. Upon leaving the inlet conduit 30A (or its constricted passage 54) the liquid flow enters the fluid-receiving chamber 32A. After said chamber 32A is substantially filled, the liquid flow enters the fluid exit conduit 36 that leads to the air vent/fluid plug device 38. Again, this device allows air to be driven from the cartridge 10B, but prevents the liquid from leaving said cartridge via the air vent/fluid plug 38.

FIG. 14 also illustrates how two distinct kinds of test can be conducted in the cartridges of this patent disclosure. The first type of test is depicted by the penetration of a wave-like line 68 into the chamber 32. This wave-like line is intended to depict electromagnetic energy of various kinds. Such energy can be used to detect various attributes of a liquid residing in the chamber 32. Again a wide variety of tests for viscosity, translucence, color, electrical conductivity, optical density, chemical component concentration, etc. can be conducted by exposing the sample to various forms of electromagnetic energy. One or more different forms of electromagnetic energy 68 can be produced by a test machine such as the test machine 12 depicted in FIG. 1. One or more different forms of electromagnetic energy also can be directed at one or more chambers 30A, 30B, 30C, etc. in a cartridge. They also can be directed at different chambers simultaneously, or they can be directed at the same chamber (e.g., chamber 32A of FIG. 14) sequentially.

Again, a particularly preferred type of test in the practice of this invention involves detection of the portion of a ferromagnetic washer 46 such as that shown in FIGS. 9 and 10. Again, movement of such a washer 46 through a liquid whose viscosity changes (as a result of contact with a viscosity altering reagent) can form the basis of various tests. Once again, applicants will use movement of such a washer 46 through a blood sample as a representative use of the cartridges of this patent disclosure. In such a test, a ferromagnetic object (such as one made of iron, nickel, cobalt, and numerous alloys known to the art) can be placed in at least one, but preferably in each of several fluid-receiving chambers 32A, 32B, 32C, etc., in a given cartridge. Such a ferromagnetic object may act both to induce and to measure viscosity changes in the fluid. In one preferred embodiment, this ferromagnetic object is a single piece such as a washer made of steel or other iron-based alloy. Such a washer is depicted in FIGS. 9 and 10. To ensure accurate and reliable results of the analytical tests, each such washer 46 should meet strict specifications, especially as to its physical measurements. Although the ferromagnetic object 46 used in this preferred embodiment will normally be a steel or other iron-based alloy washer, it should be understood that other magnetically affected materials, having other physical shapes, are within the scope of the present invention. Hence, references herein to "washers" may include other materials and shapes. Indeed, ferromagnetic objects can be introduced to in liquid sample in the form of beads, large particles, or even filings. The essential attribute is that the ferromagnetic object be freely movable in the fluid within the fluid-receiving chamber 32. Such a ferromagnetic object can be moved under the action of a magnet or by other means, for example, by the force of gravity. In any case, the ferromagnetic object most preferably will not have a large volume relative to the volume of the fluid-receiving chamber 38. In the context of blood testing, applicants have found that if a ferromagnetic washer 46 is employed, it should preferably displace a volume of about 10 $\mu$l to about 50 $\mu$l. Thus, the volume of the liquid sample that can be injected into a given fluid-receiving chamber 32 is preferably about 50 $\mu$l to about 240 $\mu$l, based on a total fluid chamber volume of about 100 $\mu$l to about 250 $\mu$l. As was previously noted, one particularly preferred embodiment of this invention employs a ferromagnetic washer 46 having a center hole in which a guide post 48 is positioned to guide the washer substantially straight up and straight down in the chamber 32.

In a blood viscosity test, a viscosity-altering reagent will preferably be placed within the cartridge between the injection port 24 and the fluid-receiving chamber 32 (e.g., in the injection port itself, in the fluid receiving/dispensing reservoir or in a conduit that connects the fluid receiving/dispensing channel). Again, a highly preferred location is in a constricted passage of a conduit located between the fluid receiving/dispensing reservoir and the fluid receiving chamber. In the case of a heparin/protamine test, for example, a different amount of protamine, which is a heparin neutralizer, can be placed within a constricted passage of each of several conduits before a heparinized blood sample is introduced into the cartridge. The blood mixes with the protamine as it travels through a given conduit system. After the blood fills the fluid receiving chamber(s), the test apparatus proceeds to raise the ferromagnetic object in one or more of the fluid-receiver chambers and then repeatedly measures one or more fall characteristics (e.g., changes in fall times) of that ferromagnetic object through the blood sample. Useful inferences are then made from such fall times (relative to some standard and/or relative to fall times in different chambers within the system). For example, the chamber in which blood clots first is the chamber in which the protamine level is closest to the heparin level of the blood sample.

It also should be understood that different amounts or more than one type of viscosity-altering substance may be used in each conduit 30A, 30B, 30C, etc. For example, in a heparin/protamine test of human blood, each such conduit may receive a different amount of protamine and, if desired, one or more different viscosity-altering substances (for example, a clotting activator such as tissue thromboplastin) in addition to the protamine. Those skilled in this art also will appreciate that several viscosity-altering substances can serve to decrease the tendency of blood to coagulate. They include, but are not limited to, heparin, warfarin, dicumarol, acenocoumarol, phenprocoumon, diphenadione, phenindione, sodium citrate, citric acid, citrate dextrose, citrate phosphate dextrose, aspirin, and edetate disodium. Viscosity-altering substances that act to increase the tendency of blood to coagulate include, but are not limited to, protamine, platelet-activating factor, factor VIII, factor IX complex, factor XVII, fibrinogen, aminocaproic acid, thrombin, thromboplastin, vitamin K, calcium chloride, kaolin, and diatomaceous earth.

As an example of such usage for a heparin/protamine test, in which the fluid sample to be analyzed is heparinized human blood, the viscosity-altering substance 56 will be protamine. A certain amount of protamine will neutralize the activity of an equivalent amount of heparin, thereby permitting the heparinized blood to clot. Thus, to prepare a cartridge 10 for a heparin/protamine test, a different amount of protamine can be placed in each of the conduits 30A, 30B, 30C, etc. The amount of protamine used can be chosen based on the probable amounts of heparin that exist in the blood sample. Thus. the cartridges 10 of this patent disclosure can be made available for a broad spectrum of surgical heparin levels. For example, when a patient is known to have a possible heparin level in his blood of between about 3 units per milliliter (ml) and 5 units per ml, in order to determine the precise amount of protamine that will be needed to neutralize the heparin in that patient's blood, the range of protamine placed into the conduits 30A, 30B, 30C, etc. may extend from less than about 3 units per ml to more than about 5 units per ml, with each conduit receiving a different amount within that range. Under such a testing strategy, the fluid-receiving chamber 32A, 32B, 32C, etc. in which clotting is first observed is that chamber in which the amount of protamine is closest to the amount of heparin activity in the blood that is being circulated.

Although the preceding disclosure sets forth a number of embodiments of the present invention, those skilled in this art will however appreciate that other arrangements or embodiments, not precisely set forth, could be practiced under the teachings of the present invention. Therefore, the scope of this invention should only be limited by the scope of the following claims.

Thus having disclosed our invention, we claim:

1. A cartridge for use in a test for detecting a change in a property of a liquid/reagent mixture, said cartridge comprising a cartridge body having:
    an injection port for introducing a liquid into the cartridge;
    a fluid receiving/dispensing reservoir for receiving a liquid from the injection port and dispensing the liquid to at least one fluid-receiving chamber;
    at least one conduit for creating fluid communication between the fluid receiving/dispensing reservoir and at least one fluid-receiving chamber and wherein said at least one conduit further comprises a constricted passage;
    at least one fluid-receiving chamber for receiving a liquid/reagent mixture in a flow direction that is substantially tangential to an outside wall of said fluid-receiving chamber; and
    an air vent/fluid plug device in fluid communication with the fluid-receiving chamber.

2. The cartridge of claim 1 further comprising a reagent capable of changing a property of the liquid.

3. The cartridge of claim 1 further comprising a reagent located in the conduit for creating fluid communication between the fluid receiving/dispensing reservoir and a fluid-receiving chamber.

4. The cartridge of claim 1 further comprising a reagent located in the constricted passage of the conduit.

5. The cartridge of claim 1 further comprising a blood viscosity altering reagent located in the constricted passage of the conduit.

6. The cartridge of claim 1 further comprising a syringe that is used as a handle for the cartridge.

7. A cartridge for use in a test for detecting a change in a property of a liquid/reagent mixture, said cartridge comprising a cartridge body having:
    an injection port for introducing a liquid into the cartridge;
    a fluid receiving/dispensing reservoir for receiving a liquid from the injection port and dispensing the liquid to at least one fluid-receiving chamber;
    at least one conduit for creating fluid communication between the fluid receiving/dispensing reservoir and at least one fluid-receiving chamber and wherein said at least one conduit further comprises a constricted passage;
    at least one fluid-receiving chamber for receiving a liquid/reagent mixture in a incoming flow direction that is substantially tangential to an outside wall of said fluid-receiving chamber and for dispensing the liquid/reagent mixture in a outgoing flow direction that also is substantially tangential to an outside surface of said wall of the fluid-receiving chamber.

8. The cartridge of claim 7 further comprising a reagent capable of changing a property of the liquid.

9. The cartridge of claim 7 further comprising a reagent located in the conduit for creating fluid communication between the fluid receiving/dispensing reservoir and a fluid-receiving chamber.

10. The cartridge of claim 7 further comprising a reagent located in the constricted passage of the conduit.

11. The cartridge of claim 7 further comprising a blood viscosity altering reagent located in the constricted passage of the conduit.

12. The cartridge of claim 7 further comprising a syringe that is used as a handle for the cartridge.

13. A cartridge for use in a test for detecting a change in a property of a liquid/reagent mixture, said cartridge comprising a cartridge body having:
    an injection port for introducing a liquid into the cartridge;
    a fluid receiving/dispensing reservoir for receiving a liquid from the injection port and dispensing the liquid to at least one fluid-receiving chamber;
    at least one conduit for creating fluid communication between the fluid receiving/dispensing reservoir and at least one fluid-receiving chamber;
    at least one fluid-receiving chamber for receiving a liquid/reagent mixture in a flow direction that is substantially tangential to an outside wall of said fluid-receiving chamber; and
    an air vent/fluid plug device in fluid communication with the fluid-receiving chamber.

14. A cartridge for use in a test for detecting a change in a property of a liquid/reagent mixture, said cartridge comprising a cartridge body having:
    an injection port for introducing a liquid into the cartridge;

a fluid receiving/dispensing reservoir for receiving a liquid from the injection port and dispensing the liquid to at least one fluid-receiving chamber;

at least one conduit for creating fluid communication between the fluid receiving/dispensing reservoir and at least one fluid-receiving chamber;

at least one fluid-receiving chamber for receiving a liquid/reagent mixture and for dispensing the liquid/reagent mixture in an outgoing flow direction that is substantially tangential to an outside surface of said wall of the fluid-receiving chamber.

15. An apparatus for detecting changes in viscosity of human blood, said apparatus comprising:

a cartridge having a blood receiving/dispensing reservoir, six blood-receiving chambers, and six conduits each having a constricted passage that contains a blood viscosity changing reagent and a fluid flow direction that is substantially tangent to a round wall of each of said six fluid-receiving chambers;

an injection port in the cartridge for introducing blood into the blood receiving/dispensing reservoir from a syringe attached to said cartridge;

six air vent/fluid plug devices that are respectively in fluid communication with a blood-receiving chamber in a manner such that air is vented from the cartridge, but blood is prevented from leaving said cartridge via said air vent/fluid plug devices;

a ferromagnetic washer having a center hole hat surrounds a post in each of the six blood-receiving chambers such that said washer is free to move up and down within each blood-receiving chamber;

a test machine having an electromagnet for moving a ferromagnetic washer within each blood-receiving chamber; and a device for detecting the position of the ferromagnetic washer within a blood-receiving chamber.

\* \* \* \* \*